United States Patent
Kas et al.

(10) Patent No.: US 9,623,352 B2
(45) Date of Patent: Apr. 18, 2017

(54) METHOD FOR RETROVIRUS REMOVAL

(75) Inventors: Onur Y. Kas, Boston, MA (US);
Mikhail Kozlov, Lexington, MA (US);
Wilson Moya, Concord, MA (US);
Philip Goddard, Merrimack, NH (US);
Sherry Ashby Leon, Leominister, MA (US); Jibin Hao, Acton, MA (US);
Gabriel Tkacik, Bedford, MA (US)

(73) Assignee: EMD Millipore Corporation, Billerica, MA (US)

( * ) Notice: Subject to any disclaimer, the term of this patent is extended or adjusted under 35 U.S.C. 154(b) by 116 days.

(21) Appl. No.: 13/194,227

(22) Filed: Jul. 29, 2011

(65) Prior Publication Data

US 2012/0061332 A1    Mar. 15, 2012

Related U.S. Application Data

(60) Provisional application No. 61/372,243, filed on Aug. 10, 2010.

(51) Int. Cl.
*B01D 39/16* (2006.01)
*B01D 69/10* (2006.01)
(Continued)

(52) U.S. Cl.
CPC .......... *B01D 39/1607* (2013.01); *A61L 2/022* (2013.01); *B01D 39/00* (2013.01);
(Continued)

(58) Field of Classification Search
CPC ................. A61L 2/0017; A61L 2/022; C12N 2740/16051; C12N 7/00; B01D 2323/39; B01D 2239/025; B01D 2239/0631; B01D 67/0004; B01D 69/02; B01D 2239/0442; B01D 2239/1233; B01D 2325/20;
(Continued)

(56) References Cited

U.S. PATENT DOCUMENTS

| 692,631 A | 2/1902 | Cooley |
|---|---|---|
| 705,691 A | 7/1902 | Morton |

(Continued)

FOREIGN PATENT DOCUMENTS

| CN | 1471421 A | 1/2004 |
|---|---|---|
| CN | 1625429 A | 6/2005 |

(Continued)

OTHER PUBLICATIONS

English translation of WO 2010/069296 A1 (Jun. 2010).*
(Continued)

*Primary Examiner* — John Kim
(74) *Attorney, Agent, or Firm* — Foley Hoag LLP

(57) ABSTRACT

A method for removing retroviruses from liquid samples and a nanofiber containing liquid filtration medium that simultaneously exhibits high liquid permeability and high microorganism retention is disclosed. Retroviruses are removed from a liquid by passing the liquid through a porous nanofiber containing filtration medium having a retrovirus LRV greater than about 6, and the nanofiber(s) has a diameter from about 10 nm to about 100 nm. The filtration medium can be in the form of a fibrous electrospun polymeric nanofiber liquid filtration medium mat.

20 Claims, 5 Drawing Sheets

(51) Int. Cl.
  *B01D 39/04* (2006.01)
  *B01D 39/14* (2006.01)
  *B01D 39/00* (2006.01)
  *B01D 67/00* (2006.01)
  *B01D 69/02* (2006.01)
  *C12N 7/00* (2006.01)
  *A61L 2/02* (2006.01)
  *B01D 61/14* (2006.01)

(52) U.S. Cl.
  CPC ............ *B01D 39/04* (2013.01); *B01D 39/14* (2013.01); *B01D 39/16* (2013.01); *B01D 39/1615* (2013.01); *B01D 39/1623* (2013.01); *B01D 67/002* (2013.01); *B01D 67/0004* (2013.01); *B01D 69/02* (2013.01); *B01D 69/10* (2013.01); *C12N 7/00* (2013.01); *B01D 61/14* (2013.01); *B01D 2239/025* (2013.01); *B01D 2239/0442* (2013.01); *B01D 2239/0631* (2013.01); *B01D 2239/1233* (2013.01); *B01D 2323/39* (2013.01); *B01D 2323/42* (2013.01); *B01D 2325/20* (2013.01); *C12N 2740/16051* (2013.01)

(58) Field of Classification Search
  CPC ...... B01D 61/14; B01D 69/10; B01D 67/002; B01D 69/12
  USPC ....... 210/649, 650, 767, 483, 488, 489, 490, 210/500.1, 500.27, 500.36, 500.38, 210/500.41, 503, 504, 506, 508; 435/2
  See application file for complete search history.

(56) References Cited

U.S. PATENT DOCUMENTS

| | | |
|---|---|---|
| 1,699,615 A | 1/1929 | Hagiwara |
| 1,975,504 A | 10/1934 | Formhals |
| 2,048,651 A | 7/1936 | Norton |
| 2,158,415 A | 5/1939 | Formhals |
| 2,158,416 A | 5/1939 | Formhals |
| 2,160,962 A | 6/1939 | Formhals |
| 2,168,027 A | 8/1939 | Gladding |
| 2,349,950 A | 5/1944 | Formhals |
| 3,585,126 A | 6/1971 | Cannon et al. |
| 3,620,970 A | 11/1971 | Klug et al. |
| 3,864,289 A | 2/1975 | Rendall |
| 3,994,258 A | 11/1976 | Simm |
| 4,043,331 A | 8/1977 | Martin et al. |
| 4,069,026 A | 1/1978 | Simm et al. |
| 4,127,706 A | 11/1978 | Martin et al. |
| 4,143,196 A | 3/1979 | Simm et al. |
| 4,261,834 A | 4/1981 | deWinter |
| 4,323,525 A | 4/1982 | Bornat |
| 4,510,047 A | 4/1985 | Thompson |
| 4,604,326 A | 8/1986 | Manabe et al. |
| 4,629,563 A | 12/1986 | Wrasidlo |
| 4,650,506 A | 3/1987 | Barris et al. |
| 4,657,793 A | 4/1987 | Fisher |
| 4,704,324 A | 11/1987 | Davis et al. |
| 4,778,601 A | 10/1988 | Lopatin et al. |
| 4,824,568 A | 4/1989 | Allegrezza, Jr. et al. |
| 4,839,203 A | 6/1989 | Davis et al. |
| 4,853,129 A | 8/1989 | Wan |
| 4,938,869 A | 7/1990 | Bayerlein et al. |
| 4,983,288 A | 1/1991 | Karbachsch et al. |
| 5,228,994 A | 7/1993 | Tkacik et al. |
| 5,500,167 A | 3/1996 | Degen |
| 5,522,601 A | 6/1996 | Murphy |
| 5,522,991 A | 6/1996 | Tuccelli et al. |
| 5,652,050 A | 7/1997 | Pall et al. |
| 5,731,164 A | 3/1998 | Becker et al. |
| 5,739,316 A | 4/1998 | Beer et al. |
| 5,846,438 A | 12/1998 | Pall et al. |
| 5,968,650 A | 10/1999 | Tennent et al. |
| 5,985,112 A | 11/1999 | Fischer |
| 6,074,869 A | 6/2000 | Pall et al. |
| 6,113,794 A | 9/2000 | Kumar et al. |
| 6,153,098 A | 11/2000 | Bayerlein et al. |
| 6,321,915 B1 | 11/2001 | Wilson et al. |
| 6,554,881 B1 | 4/2003 | Healey |
| 6,598,749 B2 | 7/2003 | Paul et al. |
| 6,604,925 B1 | 8/2003 | Dubson |
| 6,713,011 B2 | 3/2004 | Chu et al. |
| 6,743,273 B2 | 6/2004 | Chung et al. |
| 6,746,517 B2 | 6/2004 | Benson et al. |
| 6,770,204 B1 | 8/2004 | Koslow |
| 6,835,311 B2 | 12/2004 | Koslow |
| 6,858,057 B2 | 2/2005 | Healey |
| 6,866,704 B2 | 3/2005 | Koslow |
| 6,872,311 B2 | 3/2005 | Koslow |
| 6,913,154 B2 | 7/2005 | Koslow |
| 6,924,028 B2 | 8/2005 | Chung et al. |
| 6,953,604 B2 | 10/2005 | Koslow |
| 6,955,775 B2 | 10/2005 | Chung et al. |
| 6,959,820 B2 | 11/2005 | Koslow |
| 6,974,490 B2 | 12/2005 | Gillingham et al. |
| 6,994,811 B2 | 2/2006 | Kools |
| 6,998,058 B2 | 2/2006 | Koslow |
| 7,008,465 B2 | 3/2006 | Graham et al. |
| 7,008,537 B2 | 3/2006 | Koslow |
| 7,070,640 B2 | 7/2006 | Chung et al. |
| 7,070,836 B2 | 7/2006 | Czado |
| 7,090,712 B2 | 8/2006 | Gillingham et al. |
| 7,090,715 B2 | 8/2006 | Chung et al. |
| 7,097,694 B1 | 8/2006 | Jaroszczyk et al. |
| 7,105,228 B2 | 9/2006 | Averdung et al. |
| 7,108,791 B2 | 9/2006 | Tkacik et al. |
| 7,109,136 B2 | 9/2006 | Senecal et al. |
| 7,115,150 B2 | 10/2006 | Johnson et al. |
| 7,144,533 B2 | 12/2006 | Koslow |
| 7,179,317 B2 | 2/2007 | Chung et al. |
| 7,229,665 B2 | 6/2007 | Kools |
| 7,235,122 B2 | 6/2007 | Bryner et al. |
| 7,270,692 B2 | 9/2007 | Gillingham et al. |
| 7,270,693 B2 | 9/2007 | Chung et al. |
| 7,318,853 B2 | 1/2008 | Chung et al. |
| 7,378,020 B2 | 5/2008 | Ieraci et al. |
| 7,419,601 B2 | 9/2008 | Cooper et al. |
| 7,459,085 B2 | 12/2008 | Koguma et al. |
| 7,470,639 B2 | 12/2008 | Angelini et al. |
| 7,555,195 B2 | 6/2009 | Yamashita et al. |
| 7,585,437 B2 | 9/2009 | Jirsak et al. |
| 7,743,929 B2 | 6/2010 | Kools |
| 7,789,930 B2 | 9/2010 | Ensor et al. |
| 7,790,135 B2 | 9/2010 | Lennhoff |
| 7,875,380 B2 | 1/2011 | Chun et al. |
| 7,927,885 B2 | 4/2011 | Nishita |
| 7,993,523 B2 | 8/2011 | Chen et al. |
| 8,038,013 B2 | 10/2011 | Chen et al. |
| 8,222,166 B2 | 7/2012 | Chu et al. |
| 8,282,712 B2 | 10/2012 | Chi et al. |
| 8,361,180 B2 | 1/2013 | Lim et al. |
| 8,366,797 B2 | 2/2013 | Chung et al. |
| 8,679,217 B2 | 3/2014 | Chi et al. |
| 8,689,985 B2 | 4/2014 | Bates, III et al. |
| 9,174,152 B2 | 11/2015 | Dai et al. |
| 9,180,393 B2 | 11/2015 | Chen et al. |
| 2002/0046656 A1 | 4/2002 | Benson et al. |
| 2002/0084178 A1 | 7/2002 | Dubson et al. |
| 2002/0096246 A1 | 7/2002 | Sennet et al. |
| 2002/0100725 A1 | 8/2002 | Lee et al. |
| 2002/0124953 A1 | 9/2002 | Sennett et al. |
| 2002/0175124 A1 | 11/2002 | Tkacik et al. |
| 2003/0010002 A1 | 1/2003 | Johnson et al. |
| 2003/0026985 A1 | 2/2003 | Greiner et al. |
| 2003/0121844 A1 | 7/2003 | Koo et al. |
| 2003/0137083 A1 | 7/2003 | Ko et al. |
| 2003/0177909 A1 | 9/2003 | Koslow |
| 2003/0213218 A1 | 11/2003 | Dubson |
| 2003/0213744 A1 | 11/2003 | Kools et al. |
| 2004/0038013 A1 | 2/2004 | Schaefer et al. |
| 2004/0038014 A1 | 2/2004 | Schaefer et al. |

(56) References Cited

U.S. PATENT DOCUMENTS

| | | |
|---|---|---|
| 2004/0070118 A1 | 4/2004 | Czado |
| 2004/0080083 A1 | 4/2004 | Czado |
| 2004/0116025 A1 | 6/2004 | Gogins et al. |
| 2004/0159609 A1 | 8/2004 | Chase |
| 2004/0206693 A1 | 10/2004 | Charkoudian et al. |
| 2004/0206694 A1 | 10/2004 | Charkoudian |
| 2004/0207126 A1 | 10/2004 | Czado |
| 2005/0026526 A1 | 2/2005 | Verdegan et al. |
| 2005/0048274 A1 | 3/2005 | Rabolt et al. |
| 2005/0051487 A1 | 3/2005 | Koslow |
| 2005/0053782 A1 | 3/2005 | Sen et al. |
| 2005/0067732 A1 | 3/2005 | Kim et al. |
| 2005/0073075 A1 | 4/2005 | Chu et al. |
| 2005/0142973 A1 | 6/2005 | Bletsos et al. |
| 2005/0163955 A1 | 7/2005 | Schaefer et al. |
| 2005/0210844 A1 | 9/2005 | Kahlbaugh et al. |
| 2005/0235619 A1 | 10/2005 | Heinz et al. |
| 2005/0247236 A1 | 11/2005 | Frey et al. |
| 2005/0272925 A1 | 12/2005 | Charkoudian et al. |
| 2006/0057377 A1 | 3/2006 | Harrison et al. |
| 2006/0060519 A1 | 3/2006 | Tkacik et al. |
| 2006/0068668 A1 | 3/2006 | Kameoka et al. |
| 2006/0084340 A1 | 4/2006 | Bond et al. |
| 2006/0084341 A1 | 4/2006 | Bodaghi et al. |
| 2006/0094320 A1 | 5/2006 | Chen et al. |
| 2006/0096912 A1 | 5/2006 | Nussbaumer et al. |
| 2006/0097431 A1 | 5/2006 | Hovanec |
| 2006/0135020 A1 | 6/2006 | Weinberg et al. |
| 2006/0137317 A1 | 6/2006 | Bryner et al. |
| 2006/0137318 A1 | 6/2006 | Lim et al. |
| 2006/0138710 A1 | 6/2006 | Bryner et al. |
| 2006/0138711 A1 | 6/2006 | Bryner et al. |
| 2006/0160064 A1 | 7/2006 | Carbonell |
| 2006/0213829 A1 | 9/2006 | Rutledge et al. |
| 2006/0230731 A1 | 10/2006 | Kalayci et al. |
| 2006/0246798 A1 | 11/2006 | Reneker et al. |
| 2006/0264139 A1 | 11/2006 | Czado |
| 2006/0264140 A1 | 11/2006 | Andrady et al. |
| 2006/0286886 A1 | 12/2006 | Komura et al. |
| 2006/0290031 A1 | 12/2006 | Jirsak et al. |
| 2006/0293169 A1 | 12/2006 | Srinivasan et al. |
| 2007/0009736 A1 | 1/2007 | Chuang et al. |
| 2007/0018361 A1 | 1/2007 | Xu |
| 2007/0021021 A1 | 1/2007 | Verdegan et al. |
| 2007/0040305 A1 | 2/2007 | Armantrout et al. |
| 2007/0042069 A1 | 2/2007 | Armantrout |
| 2007/0062855 A1 | 3/2007 | Chase et al. |
| 2007/0074628 A1 | 4/2007 | Jones et al. |
| 2007/0075015 A1 | 4/2007 | Bates, III et al. |
| 2007/0084786 A1 | 4/2007 | Smithies |
| 2007/0113530 A1 | 5/2007 | Morozov et al. |
| 2007/0125700 A1 | 6/2007 | Ding et al. |
| 2007/0134151 A1 | 6/2007 | Jo et al. |
| 2007/0151921 A1 | 7/2007 | Nakano et al. |
| 2007/0163217 A1 | 7/2007 | Frey et al. |
| 2007/0175196 A1 | 8/2007 | Tepper et al. |
| 2007/0196401 A1 | 8/2007 | Naruse et al. |
| 2007/0240576 A1 | 10/2007 | von Blucher et al. |
| 2007/0298072 A1 | 12/2007 | Kitazono et al. |
| 2008/0004205 A1 | 1/2008 | Tkacik et al. |
| 2008/0010959 A1 | 1/2008 | Gillingham et al. |
| 2008/0026041 A1 | 1/2008 | Tepper et al. |
| 2008/0034967 A1 | 2/2008 | Ping |
| 2008/0060328 A1 | 3/2008 | Devine |
| 2008/0070463 A1 | 3/2008 | Arora et al. |
| 2008/0073296 A1 | 3/2008 | Dema et al. |
| 2008/0099398 A1 | 5/2008 | Hu et al. |
| 2008/0110342 A1 | 5/2008 | Ensor et al. |
| 2008/0110822 A1 | 5/2008 | Chung et al. |
| 2008/0134652 A1 | 6/2008 | Lim et al. |
| 2008/0136063 A1 | 6/2008 | Chuang et al. |
| 2008/0149561 A1 | 6/2008 | Chu et al. |
| 2008/0150197 A1 | 6/2008 | Chang et al. |
| 2008/0164214 A1 | 7/2008 | Lerner et al. |
| 2008/0207076 A1 | 8/2008 | Jirsak et al. |
| 2008/0213574 A1 | 9/2008 | McKee et al. |
| 2008/0217239 A1 | 9/2008 | Chen et al. |
| 2008/0217241 A1 | 9/2008 | Smithies et al. |
| 2008/0217807 A1 | 9/2008 | Lee et al. |
| 2008/0220241 A1 | 9/2008 | Abdelsalam et al. |
| 2008/0237934 A1 | 10/2008 | Reneker et al. |
| 2008/0242171 A1 | 10/2008 | Huang et al. |
| 2008/0264258 A1 | 10/2008 | Mares et al. |
| 2008/0264259 A1 | 10/2008 | Leung |
| 2008/0274312 A1 | 11/2008 | Schelling et al. |
| 2008/0284050 A1 | 11/2008 | Mares et al. |
| 2009/0026137 A1 | 1/2009 | Chen et al. |
| 2009/0199717 A1 | 8/2009 | Green et al. |
| 2010/0139224 A1 | 6/2010 | Lim et al. |
| 2010/0193428 A1 | 8/2010 | Hane et al. |
| 2010/0206803 A1 | 8/2010 | Ward et al. |
| 2010/0316988 A1 | 12/2010 | Sehgal |
| 2011/0163035 A1 | 7/2011 | Cheng et al. |
| 2011/0198282 A1 | 8/2011 | Chu et al. |
| 2011/0233152 A1 | 9/2011 | Wieczorek et al. |
| 2011/0305872 A1 | 12/2011 | Li et al. |
| 2012/0061332 A1 | 3/2012 | Kas et al. |
| 2012/0091072 A1 | 4/2012 | Kozlov et al. |
| 2013/0092622 A1 | 4/2013 | Kas et al. |
| 2014/0116945 A1 | 5/2014 | Kas et al. |
| 2015/0298070 A1 | 10/2015 | Koslov et al. |
| 2015/0360157 A1 | 12/2015 | Hwang et al. |
| 2016/0016124 A1 | 1/2016 | Zheng et al. |
| 2016/0136558 A1 | 5/2016 | Zheng et al. |
| 2016/0136584 A1 | 5/2016 | Hwang et al. |
| 2016/0166961 A1 | 6/2016 | Haberkamp et al. |
| 2016/0175748 A1 | 6/2016 | Park |
| 2016/0193555 A1 | 7/2016 | Park |

FOREIGN PATENT DOCUMENTS

| | | |
|---|---|---|
| CN | 101272840 A | 9/2008 |
| CN | 101318090 A | 12/2008 |
| CN | 102227247 A | 10/2011 |
| CN | 102917777 A | 2/2013 |
| DE | 19545701 C1 | 5/1997 |
| EP | 0257635 A2 | 3/1988 |
| EP | 0320033 A1 | 6/1989 |
| EP | 0497594 A1 | 8/1992 |
| EP | 0781600 A2 | 7/1997 |
| EP | 1743975 A1 | 1/2007 |
| EP | 1745808 A1 | 1/2007 |
| EP | 1829603 A1 | 9/2007 |
| EP | 1878482 A1 | 1/2008 |
| EP | 1673493 B1 | 7/2009 |
| EP | 2174703 A1 | 4/2010 |
| EP | 2222385 B1 | 9/2010 |
| EP | 2599908 A1 | 6/2013 |
| JP | 2-161954 A | 6/1990 |
| JP | 4-351645 A | 12/1992 |
| JP | 2000-61277 A | 2/2000 |
| JP | 2000-325764 A | 11/2000 |
| JP | 2005-515880 A | 6/2005 |
| JP | 2005-270965 A | 10/2005 |
| JP | 2005-536347 A | 12/2005 |
| JP | 2006-326579 A | 12/2006 |
| JP | 2007-332342 A | 12/2007 |
| JP | 2008-162098 A | 7/2008 |
| JP | 2009-509754 A | 3/2009 |
| JP | 2009-148748 A | 7/2009 |
| JP | 2010-94962 A | 4/2010 |
| JP | 2012-520761 A | 9/2012 |
| JP | 2012-523320 A | 10/2012 |
| KR | 10-2005-0077304 A | 8/2005 |
| KR | 10-2006-0079211 A | 7/2006 |
| KR | 10-0871440 B1 | 12/2008 |
| KR | 10-2010-0037055 A | 4/2010 |
| WO | 97/20622 A1 | 6/1997 |
| WO | 01/14047 A1 | 3/2001 |
| WO | 03/016601 A1 | 2/2003 |
| WO | 03/064013 A1 | 8/2003 |
| WO | 03/080905 A1 | 10/2003 |
| WO | 2004/018079 A2 | 3/2004 |
| WO | 2005/024101 A1 | 3/2005 |

(56) References Cited

FOREIGN PATENT DOCUMENTS

| | | | |
|---|---|---|---|
| WO | 2006/068100 | A1 | 6/2006 |
| WO | 2006/131081 | A1 | 12/2006 |
| WO | 2007/001405 | A2 | 1/2007 |
| WO | 2007/041311 | A2 | 4/2007 |
| WO | 2007/054039 | A1 | 5/2007 |
| WO | 2007/054040 | A2 | 5/2007 |
| WO | 2007/054040 | A3 | 8/2007 |
| WO | 2007/111477 | A1 | 10/2007 |
| WO | 2007/137530 | A2 | 12/2007 |
| WO | 2008/034190 | A1 | 3/2008 |
| WO | 2008/073507 | A2 | 6/2008 |
| WO | 2008/106903 | A2 | 9/2008 |
| WO | 2008/109117 | A1 | 9/2008 |
| WO | 2009/010020 | A2 | 1/2009 |
| WO | 2009/017086 | A1 | 2/2009 |
| WO | 2009/032040 | A1 | 3/2009 |
| WO | 2009/064767 | A2 | 5/2009 |
| WO | 2009/071909 | A1 | 6/2009 |
| WO | 2010/042647 | A2 | 4/2010 |
| WO | 2010/069296 | A1 | 6/2010 |
| WO | 2010/107503 | A1 | 9/2010 |
| WO | 2010/120668 | A1 | 10/2010 |
| WO | 2011/019686 | A1 | 2/2011 |
| WO | 2011/151314 | A1 | 12/2011 |
| WO | 2012/021308 | A2 | 2/2012 |
| WO | 2012/135679 | A9 | 10/2012 |
| WO | 2013/013241 | A2 | 1/2013 |
| WO | 2014/093345 | A1 | 6/2014 |
| WO | 2014/159124 | A1 | 10/2014 |

OTHER PUBLICATIONS

International Search Report and Written Opinion received for PCT patent Application No. PCT/US2011/045905, mailed on Mar. 19, 2012, 13 pages.
International Preliminary Report on Patentability received for PCT Patent Application No. PCT/US2011/045905, mailed on Feb. 21, 2013, 7 pages.
Aussawasathien et al., "Separation of micron to sub-micron particles from water: Electrospun nylon-6 nanofibrous membranes as pre-filters", Journal of Membrane Science, vol. 315, 2008, pp. 11-19.
Bjorge et al., "Performance assessment of electrospun nanofibers for filter applications", Desalination, 2009, 7 pages.
Gopal et al., "Electrospun nanofibrous polysulfone membranes as pre-filters: Particulate removal", Journal of Membrane Science, vol. 289, 2007, pp. 210-219.
Meltzer et al., "Filtration and Purification in the Biopharmaceuticals Industry: Ensuring Safety of Biopharmaceuticals Virus and Prior Safety Considerations", 2nd edition, Informa Healthcare USA, Inc., Chapter 20, 2008, pp. 543-577.
International Search Report and Written Opinion received for PCT Patent Application No. PCT/US2012/031549, mailed on Nov. 28, 2012, 15 pages.
International Preliminary Report on Patentability received for PCT Patent Application No. PCT/US012/031549, mailed on Oct. 10, 2013, 10 pages.
Galka, et al., "Life Sciences: Trends in Biopharmaceutical Filtration and Clarification", Filtration & Separation, vol. 44, No. 3, Apr. 2007, pp. 18-21.
Database WPI, "Week 200935", Thomson Scientific London, GB, 2009-F08014; XP002726900, 2 pages.
Japanese communication, with English translation, mailed Apr. 7, 2015 in co-pending Japanese patent application No. 2014-521858.
ASTM International, Designation: D1777, Reapproved 2011, "Standard Test Method for Thickness of Textile Materials", 5 pages.
Journal of Membrane Science, 2006, vol. 283, pp. 209-218, "Preparation and characterization of nanofibrous filtering media", Barhate, et al.
Journal of Membrane Science, 2007, vol. 296, pp. 1-8, "Nanofibrous filtering media: Filtration problems and solutions from tiny materials", Barhate, et al.
Advanced Functional Materials, 2008, vol. 18, pp. 2618-2624, DOI: 10.1002/adfm.200701487, "Strong, Tough, Electrospun Polymer-Nanotube Composite Membranes with Extremely Low Density", Blond, et al.
Polymer, 2001, vol. 42, pp. 261-272, "The effect of processing variables on the morphology of electrospun nanofibers and textiles", Deitzel, et al.
Journal of Electrostatics, 1995, vol. 35, pp. 151-160, "Electrospinning Process and Applications of Electrospun Fibers", Doshi, et al.
2008 2nd IEEE International Nanoelectronics Conference (INEC 2008), pp. 33-38, "Preparing Graphitic Nanoribbons from Ultrathin Electrospun Poly(methyl methacrylate) Nanofibers by Electron Beam Irradiation", Duan, et al.
Colloids and Surfaces A: Physicochemical and Engineering Aspects, 2001, vol. 187-188, pp. 469-481, "Transport properties of porous membranes based on electrospun nanofibers", Gibson, et al.
Macromolecules, 2002, vol. 35, pp. 2429-2431, "Poly (p-xylylene) Nanotubes by Coating and Removal of Ultrathin Polymer Template Fibers", Hou, et al.
Nanotechnology, 2006, vol. 17, pp. 1558-1563, "Electrospun polymer nanofibres with small diameters", Huang, et al.
Journal of the The Electrochemical Society, 2005, vol. 152(2), pp. A295-A300, "Characterization and Properties of P (VdF-HFP)-Based Fibrous Polymer Electrolyte Membrane Prepared by Electrospinning", Kim, et al.
Introduction to Modern Virology, 2007, p. 450, Blackwell Publishing Limited, Appendixes: Survey of Virus Properties, Viruses with ssDNA genomes (class 2), 5 pages, Dimmock, et al.
Conference Report from Nanocon 2010, Oct. 2010, "Water Filtration by Nanotextiles", 6 pages, Lev, et al.
J. of Supercritical Fluids, 2004, vol. 31, pp. 329-333, "Supercritical CO2-assisted electrospinning", Levit, et al.
Journal of Applied Polymer Science, 2008, vol. 107, p. 909-917, "Preparation of Poly(ether sulfone) Nanofibers by Gas-Jet/Electrospinning", Lin, et al.
Polymer News, 2005, vol. 30, No. 6, pp. 1-9, "Melt Electrospinning of Polymers: A Review", Lyons, et al.
Journal of Membrane Science, 2005, vol. 265, pp. 115-123, "Electrospun cellulose nanofiber as affinity membrane", Ma, et al.
Journal of Membrane Science, 2006, vol. 272, pp. 179-187, "Surface modified nonwoven polysulphone (PSU) fiber mesh by electrospinning: A novel affinity membrane", Ma, et al.
Polymer Engineering and Science, 2008, vol. 48, pp. 934-940, Effect of Hot-Press on Electrospun Poly(vinylidene fluoride) Membranes, Na, et al.
Journal of Power Sources, 2008, vol. 184, pp. 437-443, "Novel electrospupn poly(vinylidene fluoride-co-hexafluoropropylene)-in situ SiO2 composite membrane-based polymer electrolyte for lithium batteries", Raghavan, et al.
Advanced Drug Delivery Reviews, 2007, vol. 59, pp. 1384-1391, "Formation of fibers by electrospinning", Rutledge, et al.
Desalination, 2008, vol. 223, pp. 349-360, "Heavy metal-contaminated groundwater treatment by a novel nanofiber membrane", Sang, et al.
Journal of Hazardous Materials, 2008, vol. 153, pp. 860-866, "Filtration by a novel nanofiber membrane and alumina adsorption to remove copper(II) from groundwater", Sang, et al.
Biomaterials, 2008, vol. 29, pp. 1989-2006, "Electrospinning: Applications in drug delivery and tissue engineering", Sill, et al.
Polymer, 2005, vol. 46, pp. 2419-2423, "Continuous yarns from electrospun fibers", Smit, et al.
Polymer, 2005, vol. 46, pp. 6128-6134, "Systematic parameter study for ultra-fine fiber fabrication via electrospinning process", Tan, et al.
Nanotechnology, 2006, vol. 17, R89-R106, "A review on electrospinning design and nanofibre assemblies", Teo, et al.
Polymer, 2004, vol. 45, pp. 2977-2980, "Upward needleless electrospinning of multiple nanofibers", Yarin, et al.

(56) References Cited

OTHER PUBLICATIONS

Polymer, 2006, vol. 47, pp. 2434-2441, "High flux ultrafiltration membranes based on electrospun nanofibrous PAN scaffolds and chitosan coating", Yoon, et al.
Biosensors and Bioelectronics, 2008, vol. 23, pp. 1208-1215, "Selective molecular adsorption using electrospun nanofiber affinity membranes", Yoshimatsu, et al.
Chemical Engineering Science, 2007, vol. 62, pp. 4751-4759, "Nanoparticle filtration by electrospun polymer fibers", Yun, et al.
Journal of Applied Polymer Science, 2005, vol. 97, pp. 466-474, "Preparation and Properties of Electrospun Poly (Vinylidene Fluoride) Membranes", Zhao, et al.
Office Action mailed Mar. 24, 2015 in co-pending U.S. Appl. No. 13/436,043.
ASTM International, Designation: F316-03 (Reapproved 2011), Standard Test Methods for Pore Size Characteristics of Membrane Filters by Bubble Point and Mean Flow Pore Test, 2011, 7 pages.
ASTM International, Designation: F838-15, Standard Test Method for Determining Bacterial Retention of Membrane Filters Utilized for Liquid Filtration, 2015, 6 pages.
International Preliminary Report on Patentability mailed Jun. 25, 2015 in co-pending PCT application No. PCT/US2013/074132.
ASTM International, Designation: D 1777-64, Reapproved 1975, "Standard Method for Thickness of Textile Materials", p. 477-478.
International Search Report and Written Opinion mailed Aug. 16, 2010 in co-pending PCT application No. PCT/US2010/000826.
International Preliminary Report on Patentability mailed Sep. 29, 2011 in co-pending PCT application No. PCT/US2010/000826.
International Search Report and Written Opinion mailed Feb. 26, 2013 in co-pending PCT application No. PCT/US2012/047865.
International Preliminary Report on Patentability mailed Jan. 30, 2014 in co-pending PCT application No. PCT/US2012/047865.
Japanese communication, with English translation, mailed Mar. 18, 2014 in corresponding Japanese patent application No. 2013-524096.
ASTM International, ASTM E1294-89 (1999) Withdrawal Notice, Withdrawn Standard, Standard Test Method for Pore Size Characteristics of Membrane Filters Using Automated Liquid Porosimeter (Withdrawn 2008), p. 1.
ASTM International, Designation: F316-03, 2003, Standard Test Methods for Pore Size Characteristics of Membrane Filters by Bubble Point and Mean Flow Pore Test, pp. 1-7.
ASTM International, Designation: F838-05, 2005, Standard Test Method for Determining Bacterial Retention of Membrane Filters Utilized for Liquid Filtration, pp. 1-6.
Mycoplasma—Recent Developments in Detecting and in Preventing Bioreactor Contamination, 2005, ISPE Annual Meeting, Scottsdale, Arizona, Nov. 6-10, 2005, Slides 1-38, 38 pages, Blackwell.
BioProcess International, vol. 5, No. 5, May 2007, pp. 44-51, "Quantifying Sterilizing Membrane Retention Performance", Blanchard.
Nano Letters, 2005, vol. 5, No. 5, pp. 913-916, "Collecting Electrospun Nanofibers with Patterned Electrodes", Li, et al.
In Filtration in the Pharmaceutical Industry, Marcel Dekker, NY, 1987, p. 103, Filter Porosity Characteristics, 3.2.2 Narrow Pore-Size Distribution of Inverse-Phase Membranes, Meltzer.
Biopharm, vol. 5 No. 3, Apr. 1992, pp. 22-23, "Methods Used to Validate Microporous Membranes for the Removal of Mycoplasma", Roche, et al.
Journal of Membrane Science, vol. 392-393, 2012, pp. 167-174, "Electrospun nanofibrous membranes for high flux microfiltration", Wang, et al.
Office Action mailed Dec. 13, 2013 in co-pending U.S. Appl. No. 13/257,501.
Final Rejection mailed Aug. 7, 2014 in co-pending U.S. Appl. No. 13/257,501.
Office Action mailed Oct. 23, 2013 in co-pending U.S. Appl. No. 13/436,043.
Final Rejection mailed Apr. 30, 2014 in co-pending U.S. Appl. No. 13/436,043.
English translation of Japanese communication, dated Apr. 11, 2016 in co-pending Japanese patent application No. 2014-502850.
Korean communication, with English translation, dated Mar. 28, 2016 in co-pending Korean patent application No. 10-2013-7031748.
Chinese communication, with English translation, dated Feb. 29, 2016 in co-pending Chinese patent application No. 201380070873.3
International Search Report and Written Opinion mailed Sep. 15, 2015, in co-pending PCT application No. PCT/US2015/037055.
Office action mailed Sep. 30, 2015 in co-pending U.S. Appl. No. 13/257,501.
Final rejection mailed Oct. 14, 2015 in co-pending U.S. Appl. No. 13/436,043.
Office action mailed Apr. 12, 2016 in co-pending U.S. Appl. No. 14/118,490.
Extended European Search Report received for EP Patent Application No. 07114167.5, mailed on Nov. 6, 2007, 7 pages.
Extended European Search Report received for EP Patent Application No. 10181774.0, mailed on Nov. 25, 2010, 5 pages.
Bhanushali et al., "Advances in Solvent-Resistant Nanofiltration Membranes: Experimental Observations and Applications", Annals of the New York Academy of Sciences, vol. 984, Mar. 2003, pp. 159-177.
Ebert et al., "Solvent Resistant Nanofiltration Membranes in Edible Oil Processing", Membrane Technology, vol. 107, 1999, pp. 5-8.
Granath et al., "Molecular Weight Distribution Analysis by Gel Chromatography on Sephadex", Journal of Chromatography A, vol. 28, 1967, pp. 69-81.
Guo et al., "Cellulose Membrane used as Stationary Phase of Membrane Affinity Chromatography", Chinese Chemical Letters, vol. 5, No. 10, 1994, pp. 869-872.
International Search Report and Written Opinion Received for PCT Application No. PCT/US2016/018146, mailed on Jun. 7, 2016, 11 pages.
Zeman et al., "Steric Rejection of Polymeric Solutes by Membranes with Uniform Pore Size Distribution", Separation Science and Technology, vol. 16, No. 3, Apr. 1981, pp. 275-290.
Zwijnenberg et al., "Acetone-Stable Nanofiltration Membranes in Deacidifying Vegetable Oil", Journal of the American Oil Chemist's Society, vol. 76, No. 1, 1999, pp. 83-87.

* cited by examiner

METHOD FOR RETROVIRUS REMOVAL

CROSS-REFERENCED TO RELATED APPLICATION

The present application claims the benefit of priority of U.S. Provisional Patent Application No. 61/372,243, filed on Aug. 10, 2010, the entire content of which is incorporated by reference herein in its entirety.

FIELD OF THE INVENTION

The present invention relates generally to liquid filtration media. In certain embodiments, the invention provides a porous electrospun nanofiber liquid filtration mat and methods of using the same in the retention of retroviruses from a filtered liquid.

BACKGROUND OF THE INVENTION

Regulatory agencies around the world place stringent requirements on commercial manufacturers of biopharmaceutical compounds to provide biosafety assurance of their drugs. The manufacturers have to build in and validate at least two orthogonal steps, i.e. operating by two distinct mechanisms, of virus removal into their processes, one of which is usually size-based filtration. The combined LRV (log reduction value) for retrovirus removal of all removal steps of the combined purification process must be at least 17, of which filtration provides at least 6.

Retrovirus is a type of RNA virus (such as HIV) that reproduces by transcribing itself into DNA (using reverse transcriptase). The resultant DNA inserts itself into a cell's DNA and is reproduced by the cell. Two particularly dangerous retroviruses to humans are Human Immunodeficiency Virus (HIV) and Human T-Cell Leukemia Virus (HTLV). The size of retroviruses falls in the range from about 80 to 130 nm. In development of virus-retentive filtration products, it is common practice to substitute mammalian viruses for bacteriophages of similar size, shape, and surface charge. Examples of such bacteriophages include Phi-6 and PR772. Practice shows that filters exhibiting a certain level of retention with these bacteriophages usually exhibit same or higher levels of retention with mammalian retroviruses.

A detailed description of industry approaches to virus removal and a list of commercially available virus removal products is available in "Filtration and Purification in the Biopharmaceutical Industry" by T. Meltzer and M. Jornitz, eds., $2^{nd}$ edition, Informa Healthcare USA, Inc., 2008, Chapter 20, pp. 543-577.

There are a number of commercially available membranes validated for retrovirus removal. A typical retrovirus removal membrane, for example the Retropore® available from Millipore Corporation of Billerica, Mass. The membrane has been extensively tested using the 78 nm diameter bacteriophage Phi 6. This bacteriophage is readily grown to monodispersed, uniform size, and high titer challenges. A consistent >6.5 LRV has been observed over the range of feedstock and processing conditions. The Retropore® membrane is manufactured according to U.S. Pat. No. 7,108,791, which is fully incorporated herein by reference. The Retropore® membrane has an asymmetrical pore structure, with a tight virus removal side and microporous "support" side, and is manufactured by a traditional phase inversion process used to make a wide range of UF and MF membranes.

One of the inherent limitations of this process is that porosity decreases with decrease in pore size. For example, a microporous membrane with average pore size of about 0.5 micron may have a porosity about 75% to 80%, while an ultrafiltration membrane having an average pore size of about 0.01 micron to 0.02 micron will only be about 5% to 30% porous in its region of narrowest pore size. Retrovirus removal membranes have traditionally low porosity and thus lower flux. U.S. Pat. No. 7,108,791 defines minimum desirable flux of a "large virus" (>75 nm) filter as having a minimum value of 5 to 20 lmh/psi.

U.S. Pat. No. 7,459,085 to Asahi Kasei Medical Co., Ltd., discloses a hydrophilic microporous membrane comprising a thermoplastic resin having a maximum pore size of 0 to 100 nm and designed for low protein fouling in virus filtration application.

Published US Pat. App. 2008/0004205 to Millipore Corp. discloses an integral multilayered composite membrane having at least one ultrafiltration layer designed for virus removal ultrafiltration membranes and methods of making such membrane.

As biopharmaceutical manufacturing becoming more mature, the industry is constantly looking for ways to streamline the operations, combine and eliminate steps, and dramatically reduce the time it takes to process each batch of the drug. At the same time, there are market and regulatory pressures requiring manufacturers to reduce their costs. Since virus filtration accounts for a significant percentage of the total cost of drug purification, any approaches to increase membrane throughput and reduce time are valuable. With the introduction of new prefiltration media and corresponding increase in throughput of virus filters, filtration of more and more feed streams is becoming flux-limited. Thus, dramatic improvements in the permeability of virus filters will have a direct effect on the cost of virus filtration step.

Filters used in liquid filtration can be generally categorized as either fibrous nonwoven media filters or porous film membrane filters.

Fibrous nonwoven liquid filtration media include, but are not limited to, nonwoven media formed from spunbonded, melt blown or spunlaced continuous fibers; hydroentangled nonwoven media formed from carded staple fiber and the like; or some combination of these types. Typically, fibrous nonwoven filter media filters used in liquid filtration have pore sizes generally greater than about 1 micron (µm).

Porous film membrane liquid filtration media is used either unsupported or used in conjunction with a porous substrate or support. Porous filtration membranes have pore sizes smaller than the fibrous nonwoven media, and typically have pore sizes less than about 1 µm. Porous film liquid filtration membranes can be used in: (a) microfiltration, wherein particulates filtered from a liquid are typically in the range of about 0.1 µm to about 10 µm; (b) ultrafiltration, wherein particulates filtered from a liquid, are typically in the range of about 5 nm to about 0.1 µm; and (c) reverse osmosis, wherein particulate matter filtered from a liquid, are typically in the range of about 1 Å to about 1 nm. Retrovirus-retentive membranes are usually considered to be on the open end of ultrafiltration membranes.

The two most desired features of a liquid membrane are high permeability and reliable retention. Naturally, there is a trade-off between these two parameters, and for the same type of membrane, greater retention can be achieved by sacrificing permeability of the membrane. The inherent limitations of the conventional processes for making porous film membranes prevent membranes from exceeding a certain threshold in porosity, and thus limits the magnitude of permeability that can be achieved at a given pore size.

Electrospun nanofiber mats are highly porous polymeric materials, wherein the "pore" size is linearly proportional to the fiber diameter, while the porosity is relatively independent of the fiber diameter. The porosity of electrospun nanofiber mats usually falls in the range of about 85% to 90%, and resulting in nanofiber mats demonstrating dramatically improved permeability as compared to immersion cast membranes having a similar thickness and pore size rating. Moreover, this advantage becomes amplified in the smaller pore size range, such as that typically required for virus filtration, because of the reduced porosity of UF membranes discussed supra.

The random nature of electrospun mat formation has led to the general assumption that they are unsuitable for any critical filtration of liquid streams. Electrospun nanofiber mats are often referred to as "non-wovens", thus placing them in the same category with melt-blown and spunbonded fibrous media, what is called "traditional" non-wovens.

Fibers in traditional non-wovens are usually at least about 1,000 nm in diameter, so their effective pore sizes are always more than about one micron. Also, the methods of manufacturing of traditional non-wovens lead to highly inhomogeneous fiber mats, which limits their applicability to liquid filtration.

Synthetic polymers have been formed into webs of very small diameter fibers, (i.e., on the order of a few micrometers or less than 1 μm), using various processes including melt blowing, electrostatic spinning and electroblowing. Such webs have been shown to be useful as liquid barrier materials and filters. Often they are combined with stronger sheets to form composites, wherein the stronger sheets provide the strength to meet the needs of the final filter product.

U.S. Pat. No. 7,585,437 to Jirsak teaches a nozzle-free method for producing nanofibres from a polymer solution using electrostatic spinning and a device for carrying out the method.

WIPO patent application no. WO/2003/080905, "A Manufacturing Device And Method of Preparing For The Nanofibers Via Electro-Blown Spinning Process", assigned to Nano Technics Co. LTD., and incorporated herein by reference in its entirety, teaches an electroblowing process, wherein stream of polymeric solution comprising a polymer and a solvent is fed from a storage tank to a series of spinning nozzles within a spinneret, to which a high voltage is applied and through which the polymeric solution is discharged. Meanwhile, compressed air, that may optionally be heated, is release from air nozzles disposed in the sides of, or at the periphery of the spinning nozzle. The air is directed generally downward as a blowing gas stream which envelopes and forwards the newly issued polymeric solution and aids in the formation of the fibrous web, which is collected on a grounded porous collection belt above a vacuum chamber. The electroblowing process permits formation of commercial sizes and quantities of nanowebs at basis weights in excess of about 1 gsm to great than about 40 gsm, in a relatively short time period.

U.S. Patent Publication No. 2004/0038014 issued to Schaefer et al. teaches a nonwoven filtration mat comprising one or more layers of a thick collection of fine polymeric microfibers and nanofibers formed by electrostatic spinning for filtering contaminants. The electrostatic spinning process utilizes an electro spinning apparatus including a reservoir in which the fine fiber forming polymer solution is contained, a pump and an emitter device which obtains polymer solution from the reservoir. In the electrostatic field, a droplet of the polymer solution is accelerated by the electrostatic field toward a collecting media substrate located on a grid. A high voltage electrostatic potential is maintained between the emitter and grid, with the collection substrate positioned there between, by means of a suitable electrostatic voltage source.

U.S. Patent Publication No. 2007/0075015 issued to Bates et al. teaches a liquid filtration media including at least one layer of nanofibers having average diameters less than 1,000 nanometers optionally disposed on scrim layer for filtering particulate matter in a liquid. The filtration media have flow rates of at least 0.055 L/min/cm$^2$ at relatively high levels of solidity. The media apparently has non-diminishing flow rates as differential pressures increase between 2 psi (14 kPa) and 15 psi (100 kPa).

U.S. Patent Publication No. 2009/0026137 issued to Chen teaches fabricating liquid filter with a composite medium that has a nanoweb adjacent to and optionally bonded to a microporous membrane. The membrane is characterized by an LRV value of 3.7 at a rated particle size, and the nanoweb has a fractional filtration efficiency of greater than 0.1 at the rated particle size of the membrane. The nanoweb also has a thickness efficiency ratio of greater than 0.0002 at that efficiency. The nanoweb acts to provide depth filtration to the membrane.

U.S. Pat. No. 7,144,533 to Koslow teaches s nanofiber mats coated with microbiological interception enhancing agent (such as a cationic metal complex) that provide greater than 4 LRV of viral removal and 6 LRV of bacterial removal.

U.S. Patent Publication No. 2009/0199717 to Green teaches a method to form an electrospun fiber layer carried by the substrate layer, the fine fiber layer including a significant amount of fibers with a diameter of less than 100 nanometers.

Bjorge et al. in *Desalination* 249 (2009) 942-948 teach electrospun Nylon nanofiber mats of 50-100 nm diameter and 120 um thickness. The measured bacteria LRV for non-surface treated fibers is 1.6-2.2. The authors conclude that bacteria removal efficiency of as-spun nanofiber mats is unsatisfactory.

Gopal et al. in *Journal of Membrane Science* 289 (2007) 210-219, teach electrospun polyethersulfone nanofiber mats, wherein the nanofibers have a diameter of about 470 nm, such that the during liquid filtration the mats act as a screen to filter our particles above 1 micron and as a depth filter for particles under 1 micron.

D. Aussawasathien et al. in *Journal of Membrane Science*, 315 (2008) 11-19, teach electrospun nanofibers of 30-110 nm diameter used in removal of polystyrene particles (0.5-10 um diameter).

It would be desirable to have a reliable electrospun nanofiber filter medium suitable for >99.9999% (LRV>6) removal of retroviral particles, while simultaneously achieving high permeability. These nanofiber mats would have three advantages over traditionally used virus removal membranes: (1) higher permeability as a result of higher porosity, (2) free-standing nature, (i.e., no supporting microporous structure is required), and (3) potential to be used in single layer format. The latter two advantages offer considerably greater flexibility in the design and validation of virus filtration devices.

Additionally, the porous electrospun nanofiber filtration medium would be readily scalable, adaptable to processing volumes of sample fluids ranging from milliliters to thousands of liters, and capable of use with a variety of filtration processes and devices. The invention is directed to these, as well as other objectives and embodiments.

SUMMARY OF THE INVENTION

The present invention is directed to a method of removing retroviruses from a liquid by passing the liquid through a porous electrospun nanofiber liquid filtration medium. The electrospun nanofiber liquid filtration medium can be used with or without being disposed on a porous support or substrate. The electrospun nanofiber liquid filtration medium can be formed into a variety of shapes, sizes, thicknesses and densities, such as a porous, polymeric nanofiber mat.

In another embodiment, the present invention is directed towards a porous electrospun nanofiber liquid filtration medium having a retrovirus LRV greater than about 6, and the nanofiber(s) has an average fiber diameter ranging from about 10 nm to about 100 nm.

In another embodiment, the present invention is directed towards a porous electrospun nanofiber liquid filtration medium having a retrovirus LRV greater than about 6, and the filtration medium has a porosity ranging from about 80% to about 95%.

In another embodiment, the present invention is directed towards a porous electrospun nanofiber liquid filtration medium having a retrovirus LRV greater than about 6, and a liquid permeability at 10 psi differential pressure greater than about 1,000 LMH. (Liters Per Square Meter Per Hour).

In another embodiment, the present invention is directed towards a porous electrospun nanofiber liquid filtration medium having a retrovirus LRV greater than about 6, and formed as a fibrous porous mat having a thickness ranging from about 1 µm to about 500 µm, preferably from about 1 µm to about 100 µm, or from about 1 µm to 50 µm.

In another embodiment, the present invention is directed to a process for forming a porous filtration medium from one or more electrospun polymeric nanofibers from a polymer solution by using an electrospinning apparatus, and subjecting the solution to an electric potential greater than about 10 kV, and collecting electrospun polymer fiber(s) as a non-woven mat.

In another embodiment, the present invention is directed to a composite porous filtration device comprising a filtration medium having a retrovirus LRV greater than about 6, and including an electrospun polymeric nanofiber mat disposed on a porous support or porous substrate.

Additional features and advantages of the invention will be set forth in the detailed description and claims, which follows. Many modifications and variations of this invention can be made without departing from its spirit and scope, as will be apparent to those skilled in the art. It is to be understood that the foregoing general description and the following detailed description, the claims, as well as the appended drawings are exemplary and explanatory only, and are intended to provide an explanation of various embodiments of the present teachings. The specific embodiments described herein are offered by way of example only and are not meant to be limiting in any way.

BRIEF DESCRIPTION OF THE DRAWINGS

The accompanying drawings, which are incorporated in and constitute a part of this specification, illustrate the presently contemplated embodiments of the invention and, together with the description, serve to explain the principles of the invention.

DESCRIPTION OF THE EMBODIMENTS

Figure 1:
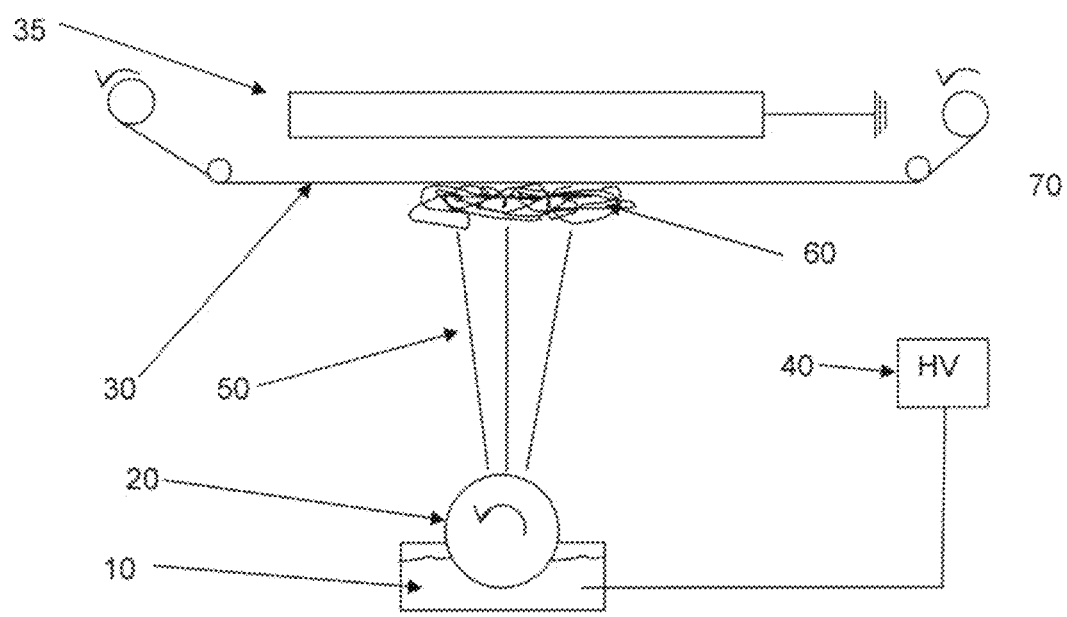
FIG. 1 is a schematic of the process of electrospinning a nanofiber according to one embodiment of the invention.

All publications, patents and patent applications cited herein, whether supra or infra, are hereby incorporated by reference in their entirety to the same extent as if each individual publication, patent or patent application was specifically and individually indicated to be incorporated by reference.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about".

Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Before describing the present invention in further detail, a number of terms will be defined. Use of these terms does not limit the scope of the invention but only serve to facilitate the description of the invention.

As used herein, the singular forms "a," "an," and "the" include plural referents unless the context clearly dictates otherwise.

The term "nanofibers" refers to fibers having diameters varying from a few tens of nanometers up to several hundred nanometers, but generally less than one micrometer.

The terms "filter medium" or "filter media" refer to a material, or collection of material, through which a fluid carrying a microorganism contaminant passes, wherein microorganism is deposited in or on the material or collection of material.

The terms "flux" and "flow rate" are used interchangeably to refer to the rate at which a volume of fluid passes through a filtration medium of a given area.

The filtration medium of the present invention includes a porous electrospun nanofiber liquid filtration mat. The nanofibers have an average fiber diameter of about 10 nm to about 100 nm. The filtration medium has a mean pore size ranging from about 0.05 um to about 1 um. The filtration medium has a porosity ranging from about 80% to about 95%. The filtration medium has a thickness ranging from about 1 µm to about 500 µm, preferably from about 10 µm and about 100 µm. The filtration medium has liquid permeability greater than about 100 LMH/psi.

Polymers suitable for use in the nanofibers of the invention include thermoplastic and thermosetting polymers. Suitable polymers include, but are not limited to, nylon, polyimide, aliphatic polyamide, aromatic polyamide, polysulfone, cellulose, cellulose acetate, polyether sulfone, polyurethane, poly(urea urethane), polybenzimidazole, polyetherimide, polyacrylonitrile, poly(ethylene terephthalate), polypropylene, polyaniline, poly(ethylene oxide), poly(ethylene naphthalate), poly(butylene terephthalate), styrene butadiene rubber, polystyrene, poly(vinyl chloride), poly(vinyl alcohol), poly(vinylidene fluoride), poly(vinyl butylene), copolymers, derivative compounds and blends thereof, and combinations thereof.

The process for making the electrospun nanofiber mat of the filtration medium is disclosed in WO 2005/024101, WO 2006/131081, and WO 2008/106903, each fully incorporated herein by reference, and each assigned to Elmarco S. R. O. of Liberec, Czech Republic.

In one embodiment of the present invention as depicted in FIG. 1, the filtration medium comprises a porous mat 60 made from a single nanofiber, wherein the single nanofiber is made by a single pass of a moving collection apparatus 30 positioned between a rotating drum 20 and a collector 35 through the electrospinning process. It will be appreciated that the fibrous web can be formed by one or more spinning drums 20 running simultaneously above the same moving collection apparatus 30.

In FIG. 1, the moving collection apparatus 30 is preferably a moving collection belt positioned within an electrostatic field 50 between the spinning drum 20 and the collector 35, wherein a polymer solution 10 can be subjected to an electrical potential from a high voltage source 40, such that an electrospun polymer fiber is produced in the electric field 50.

In one embodiment of the invention, a fibrous mat is made by depositing nanofiber (s) from a nylon solution. The nanofiber mat has a basis weight of between about 1 g/m$^2$ and about 10 g/m$^2$, as measured on a dry basis, i.e., after the residual solvent has evaporated or been removed.

In one embodiment of the invention, any of a variety of porous single or multilayered substrates or supports can be arranged on a moving collection belt to collect and combine with the electrospun nanofiber mat medium, forming a composite filtration device.

Examples of single or multilayered porous substrates or supports include, but are not limited to, spunbonded nonwovens, meltblown nonwovens, needle punched nonwovens, spunlaced nonwovens, wet laid nonwovens, resinbonded nonwovens, woven fabrics, knit fabrics, paper, and combinations thereof.

In another embodiment of the invention the electrospun nanofiber mat medium taught herein may be bonded to a porous substrate or support. Bonding may be accomplished by known methods in the art, including but not limited to thermal calendaring between heated smooth nip rolls, ultrasonic bonding, and through gas bonding. Bonding the electrospun nanofiber medium to a support increases the strength and the compression resistance of the medium, such that the medium may withstand the forces associated with being handled such as when the porous medium is formed into a useful filter and/or installed into a filtration device. In addition, the physical properties of the porous electrospun nanofiber medium such as thickness, density, and the size and shape of the pores may be affected depending on the bonding methods used.

For instance, thermal calendering can be used to reduce the thickness and increase the density and reduce the porosity of the electrospun nanofiber mat medium, and reduce the size of the pores. This in turn decreases the flow rate through the medium at a given applied differential pressure.

In general, ultrasonic bonding will bond to a smaller area of the porous electrospun nanofiber medium than thermal calendering, and therefore has a lesser effect on thickness, density and pore size.

Gas bonding generally has minimal effect on the thickness, density and pore size of the porous electrospun nanofiber medium, therefore this bonding method may be preferable in applications in which maintaining higher fluid flow rate is desired.

When thermal calendering is used, care must be taken not to over-bond the porous electrospun nanofiber material, such that the nanofibers melt and no longer retain their structure as individual fibers. In the extreme, over-bonding would result in the nanofibers melting completely such that a film would be formed. One or both of the nip rolls used is heated to a temperature of between about ambient temperature, e.g., about 25° C. and about 300° C. The porous nanofiber medium and/or porous support or substrate, can be compressed between the nip rolls at a pressure ranging from about 0 lb/in to about 1000 lb/in (178 kg/cm). The porous nanofiber medium can be compressed at a line speed of at least about 10 ft/min (3 m/min).

Calendering conditions, e.g., roll temperature, nip pressure and line speed, can be adjusted to achieve the desired solidity. In general, application of higher temperature, pressure, and/or residence time under elevated temperature and/or pressure results in increased solidity.

Other mechanical steps, such as stretching, cooling, heating, sintering, annealing, reeling, unreeling, and the like, may optionally be included in the overall process of forming, shaping and making the electrospun nanofiber mat medium as desired.

For example, the electrospun nanofiber mat medium taught herein may be stretched in a single step or a plurality of steps as desired. Depending on the stretching method used to stretch the electrospun nanofiber mat medium, stretching can adjust the physical properties of the mat including thickness, density, and the size and shape of the pores formed in the mat. For example, if the electrospun nanofiber mat is stretched in a single direction (uniaxial stretching), the stretching may be accomplished by a single stretching step or a sequence of stretching steps until the desired final stretch ratio is attained.

Similarly, if the electrospun nanofiber mat medium is stretched in two directions (biaxial stretching), the stretching can be conducted by a single biaxial stretching step or a sequence of biaxial stretching steps until the desired final stretch ratios are attained. Biaxial stretching may also be accomplished by a sequence of one or more uniaxial stretching steps in one direction and one or more uniaxial stretching steps in another direction. Biaxial stretching steps where the electrospun nanofiber mat is stretched simultaneously in two directions and uniaxial stretching steps may be conducted in sequence in any order.

Methods for stretching the mat are not particularly limited, and use may be made of ordinary tentering, rolling, or inflation or a combination of two or more of these. The stretching may be conducted uniaxially, biaxially, etc. In the case of biaxial stretching, machine-direction stretching and transverse-direction stretching may be conducted either simultaneously or successively.

Various types of stretching apparatus are well known in art and may be used to accomplish stretching of the electrospun mat according to the present invention. Uniaxial stretching is usually accomplished by stretching between two rollers wherein the second or downstream roller rotates at a greater peripheral speed than the first or upstream roller. Uniaxial stretching can also be accomplished on a standard tentering machine.

Biaxial stretching may be accomplished by simultaneously stretching in two different directions on a tentering machine. More commonly, however, biaxial stretching is accomplished by first uniaxially stretching between two differentially rotating rollers as described above, followed by either uniaxially stretching in a different direction using a tenter machine or by biaxially stretching using a tenter machine. The most common type of biaxial stretching is where the two stretching directions are approximately at right angles to each other. In most cases where a continuous sheet is being stretched, one stretching direction is at least approximately parallel to the long axis of the sheet (machine direction) and the other stretching direction is at least approximately perpendicular to the machine direction and is in the plane of the sheet (transverse direction).

After the electrospun nanofiber mat has been stretched either uniaxially or biaxially, the stretched porous electrospun nanofiber mat can again be calendared. The stretched electrospun nanofiber mat can be forwarded to a pair of heated calendar rolls acting cooperatively so as to form a mat of reduced thickness compared to the mat exiting from the stretching apparatus. By regulating the pressure exerted by these calendar rolls along with the temperature, the pore size of the final electrospun nanofiber mat can be controlled as desired, thereby allowing for the adjustment of the average pore size.

The electrospun nanofiber mat may be heated by any of a wide variety of techniques prior to, during, and/or after stretching. Examples of these techniques include radiative heating such as that provided by electrically heated or gas fired infrared heaters, convective heating such as that provided by recirculating hot air, and conductive heating such as that provided by contact with heated rolls. The temperatures which are measured for temperature control purposes may vary according to the apparatus used and personal preference.

In general, the temperature or temperatures can be controlled such that the electrospun nanofiber mat is stretched about evenly so that the variations, if any, in thickness of the stretched mat are within acceptable limits and so that the amount of stretched microporous electrospun nanofiber mat outside of those limits is acceptably low. It will be apparent that the temperatures used for control purposes may or may not be close to those of the electrospun nanofiber mat itself since they depend upon the nature of the apparatus used, the locations of the temperature-measuring devices, and the identities of the substances or objects whose temperatures are being measured.

The porosity can be modified as a result of calendering. The range of porosity from about 5% to about 90% can be obtained.

While filtration medium is often used in single-layer configuration, it is sometimes advantageous to provide more than one layer of filtration medium adjacent to each other. Layering membrane filters to improve particle retention is commonly used in virus filtration and is practiced commercially in Millipore's product lines of Viresolve® NFP and Viresolve Pro®. Layering filtration media of the same or different composition is also used to improve filter throughput. Examples of such layered filters are Millipore's Express® SHC and SHRP product lines.

Other considerations for choosing a multi-layered filtration product include economics and convenience of media and device manufacturing, ease of sterilization and validation. The fibrous filtration media of the present invention can be used in single-layer or in a multi-layer configuration.

The preferred layer configuration is often selected based on practical considerations. These considerations take into account the known relationship between LRV and thickness, whereby LRV typically increases with thickness. A practitioner can select multiple ways of achieving desired level of LRV, e.g. by using fewer layers of larger thickness or larger number of thinner layers.

Test Methods

Basis Weight was determined by ASTM D-3776, which is incorporated herein by reference and reported in $g/m^2$.

Porosity was calculated by dividing the basis weight of the sample in $g/m^2$ by the polymer density in $g/cm^3$, by the sample thickness in micrometers, multiplying by 100, and subtracting the resulting number from 100, i.e., porosity=100−[basis weight/(density.times.thickness).times.100].

Fiber Diameter was determined as follows. A scanning electron microscope (SEM) image was taken at 60,000 times magnification of each side of nanofiber mat sample. The diameter of ten (10) clearly distinguishable nanofibers were measured from each SEM image and recorded. Defects were not included (i.e., lumps of nanofibers, polymer drops, intersections of nanofibers). The average fiber diameter of both side for each sample was calculated.

Thickness was determined by ASTM D1777-64, which is incorporated herein by reference, and is reported in micrometers.

Mean flow bubble point was measured according to ASTM Designation E 1294-89, "Standard Test Method for Pore Size Characteristics of Membrane Filters Using Automated Liquid Porosimeter" by using automated bubble point method from ASTM Designation F 316 using a custom-built capillary flow porosimeter, in principle similar to a commercial apparatus from Porous Materials, Inc. (PMI), Ithaca, N.Y. Individual samples of 25 mm in diameter were wetted with isopropyl alcohol. Each sample was placed in a holder, and a differential pressure of air was applied and the fluid removed from the sample. The differential pressure at which wet flow is equal to one-half the dry flow (flow without wetting solvent) is used to calculate the mean flow pore size using supplied software.

Flow Rate (also referred to as Flux) is the rate at which fluid passes through the sample of a given area and was measured by passing deionized water through filter medium samples having a diameter of 47 (9.6 $cm^2$ filtration area) mm. The water was forced through the samples using hydraulic pressure (water head pressure) or pneumatic pressure (air pressure over water).

The effective pore size of an electrospun mat can be measured using conventional membrane techniques such as bubble point, liquid-liquid porometry, and challenge test with particles of certain size. It is known that the effective pore size of a fibrous mat generally increases with the fiber diameter and decreases with porosity.

Bubble point test provides a convenient way to measure effective pore size. It is calculated from the following equation:

$$P = \frac{2\gamma}{r} \cos\theta.$$

where P is the bubble point pressure, $\gamma$ is the surface tension of the probe fluid, r is the pore radius, and $\theta$ is the liquid-solid contact angle.

Membrane manufacturers assign nominal pore size ratings to commercial membrane filters, which are based on their retention characteristics.

Retrovirus retention was tested following a Millipore test method. The bacteriophage PR772 challenge stream was prepared with a minimum titer of $1.0 \times 10^7$ pfu/mL in a phosphate buffer saline (PBS) solution. Porous media to be tested were cut in 25 mm discs and sealed in overmolded polypropylene devices. These devices were then challenged by the above mentioned stream at 5 psi pressure after being wet by water at 25 psi pressure. The test was terminated after 100 ml of filtrate collection or after 4 hours of filtration, whichever came first. Quantification of bacteriophage in the initial and final feed were conducted on plates incubated overnight using a light box and a colony counter. Corresponding log retention values (LRV) were calculated.

The following Examples of the present invention will demonstrate that an electrospun nanofiber mat can simultaneously possess both high permeability and high bacteria retention.

Hereinafter the present invention will be described in more detail in the following examples. The invention will be further clarified by the following examples which are intended to be exemplary of the invention.

EXAMPLES

Example 1

Nanofiber layers were made by electrospinning a solution of Nylon 6 polymer. Nylon 6 was supplied by BASF Corp. Florham Park, N.J., USA, under the trademark Ultramid B24. The spinning solution was prepared as a 20% Nylon stock solution in a mixture Acetic and Formic acids (2:1 weight ratio) for 5 hours at 80° C. and the stock solution was further diluted into 13 wt. % polymer solution and solvent ratio 2:2:1 of Formic:Acetic:Water, respectively, with the necessary formic acid and water additions. The viscosity of the resulting solution is about 100 cP. The solution was immediately spun using a 6-wire spinning electrode under 82 kV electric field. An antistatically-coated non-woven material was used to support the nanofiber mat during electrospinning. The average fiber diameter of electrospun mat produced was about 25-30 nm. The spin time was 30 minutes, after which the nanofiber layer was peeled off the mat, layered and placed in overmolded devices for retention testing.

Figure 2:
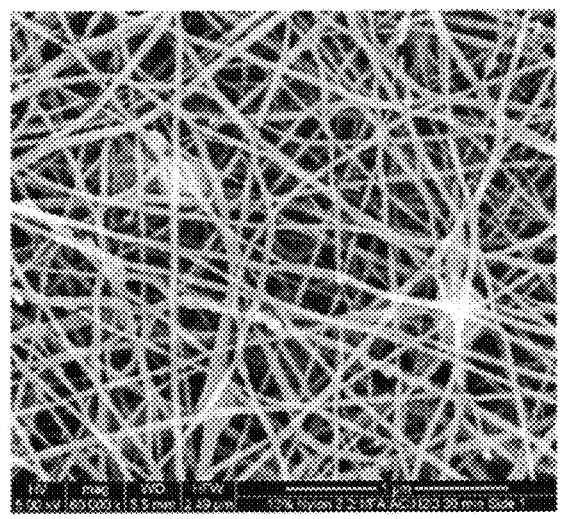
FIG. 2 is a frontal scanning electron micrograph of nylon fibers from an embodiment of the invention exemplified in Example 1.

FIG. 2 depicts a frontal scanning electron micrograph of electrospun nylon fibers exemplified in Example 1.

Table 1 displays a side by side comparison of two "fully retrovirus retentive" samples: one is a conventional immersion cast membrane (Retropore®) and the other is an electrospun nanofiber mat. Water permeability is reported for a 3 layer configuration for Retropore® and a 2 layer (30 minute spin time) configuration for the nanofiber media, since that is the corresponding number of layers typically needed to retain >6 logs of retrovirus retention.

TABLE I

Comparison of fully retentive (LRV > 6.2) samples in the device format; NFR membrane vs. electrospun nanofiber:

|  | Retropore ® membrane | Electrospun Nanofiber |
| --- | --- | --- |
| Mean flow IPA Bubble Point (psi) | 122 | 132 |
| Thickness (um) | 438* | 40** |
| Porosity (%) | 70 | 90 |
| Water Permeability (LMH/psi) | 35* | 300** |
| Retrovirus retention (LRV) | >6.2* | >6.2** |

*Measured on a three-layer membrane combination
**Measured on a two-layer mat

Figure 4:
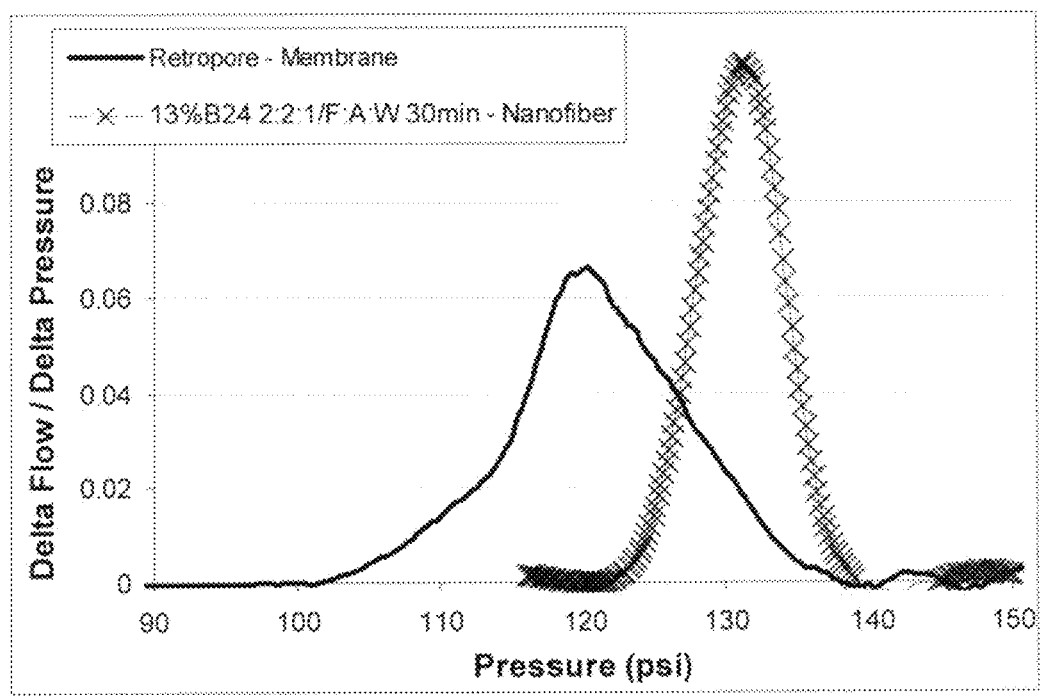
FIG. 4 is a graph of bubble point distribution for a nylon fiber mat described in Example 1 and for a commercial retrovirus retentive membrane.

FIG. 4 depicts a graph of the bubble point distribution for the nylon fiber mat embodied in Example 1 and for a commercial retrovirus retentive membrane (Retropore®).

Example 2

Figure 5:
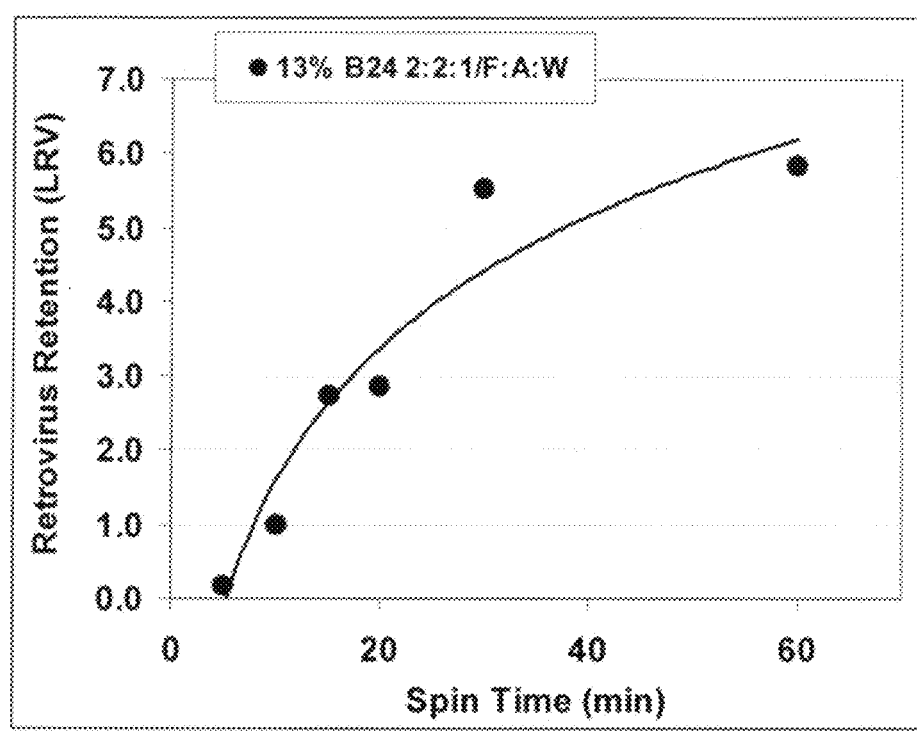
FIG. 5 is a graph of Log Reduction Value (LRV) of bacteriophage PR772 as a function of spin time of a nanofiber mat.

The procedure in Example 1 was followed. The spin time was varied from 5 to 60 minutes (FIG. 5.). PR772 retention was tested for a single layer of each nanofiber mat. Bacteriophage PR772 retention of the electrospun nanofiber mats increased with increasing spin time (increasing mat thickness).

FIG. 5 is a graph of Log Reduction Value (LRV) of bacteriophage PR772 as a function of spin time of a nanofiber mat.

Example 3

Figure 3:
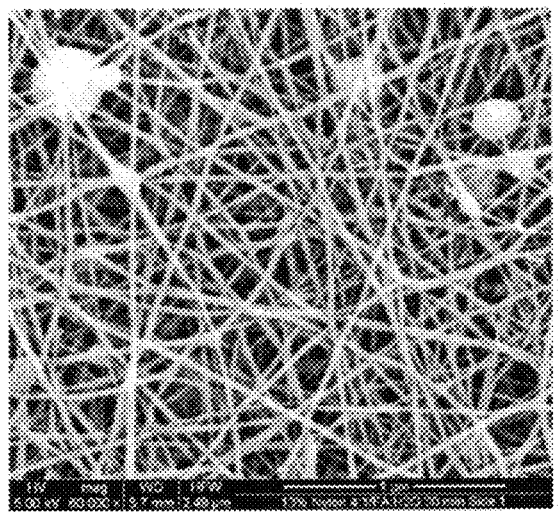
FIG. 3 is a frontal scanning electron micrograph of nylon fibers from an embodiment of the invention exemplified in Example 3.

The procedure in Example 1 was followed, with solvent system for nylon being Formic acid/Water in weight ratio 4:1. The measured fiber diameter of produced electrospun mat was in the range of 25-30 nm, and the mean IPA bubble point in the range of 120-140 psi. 30 minute spin time samples were fully retrovirus retentive (LRV for bacteriophage PR772>6.2). FIG. 3 depicts a frontal scanning electron micrograph of the nylon fibers as exemplified in Example 3.

Method of Use

Electrospun nanofiber containing liquid filtration media, in accordance with the present invention are useful in the food, beverage, pharmaceuticals, biotechnology, microelectronics, chemical processing, water treatment, and other liquid treatment industries.

Electrospun nanofiber containing liquid filtration media, in accordance with the present invention may be used for filtering, separating, identifying, and/or detecting microorganisms from a liquid sample or stream.

Electrospun nanofiber containing liquid filtration media, in accordance with the present invention may be used with any liquid sample preparation methods including, but not limited to, chromatography; high pressure liquid chromatography (HPLC); electrophoresis; gel filtration; sample centrifugation; on-line sample preparation; diagnostic kits testing; diagnostic testing; high throughput screening; affinity binding assays; purification of a liquid sample; size-based separation of the components of the fluid sample; physical properties based separation of the components of the fluid sample; chemical properties based separation of the components of the fluid sample; biological properties based separation of the components of the fluid sample; electrostatic properties based separation of the components of the fluid sample; and, combinations thereof. Also, electrospun nanofiber containing liquid filtration media, in accordance with the present invention can be component or part of a larger device and/or system.

Kits

The invention also provides kits which may be used to remove microorganisms from a liquid sample. The kit may comprise, for example, one or more electrospun nanofiber containing liquid filtration medium in accordance with the present invention, as well as one or more liquid filtration devices, support or substrate for the medium. The kit may contain one or more controls, and may optionally include various buffers useful in the methods of practicing the invention, such as wash buffers for eliminating reagents or eliminating non-specifically retained or bound material may optionally be included in the kit.

Other optional kit reagents include an elution buffer. Each of the buffers may be provided in a separate container as a solution. Alternatively the buffers may be provided in dry form or as a powder and may be made up as a solution according to the user's desired application. In this case the buffers may be provided in packets. The kit may provide a power source in instances where the device is automated as well as a means of providing an external force such as a vacuum pump. The kit may also include instructions for using the electrospun nanofiber containing liquid filtration medium, device, support or substrate, and/or for making up reagents suitable for use with the invention, and methods of practicing invention. Optional software for recording and analyzing data obtained while practicing the methods of the invention or while using the device of the invention may also be included.

The term "kit" includes, for example, each of the components combined in a single package, the components individually packaged and sold together, or the components presented together in a catalog (e.g., on the same page or double-page spread in the catalog).

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

What is claimed is:

1. A method of removing retroviruses from a liquid sample comprising the steps of:
   a) providing a liquid sample containing retroviruses,
   b) providing a filtration medium comprising a porous nanofiber mat made by electrospinning a polymer, wherein the porous nanofiber mat has a retrovirus Log Reduction Value (LRV) greater than about 6, a porosity from about 80% to about 95%, and a liquid permeability greater than about 100 LMH/psi, and wherein the nanofiber mat has a fiber diameter effective for retention of retroviruses by size-based exclusion, and
   c) passing the liquid sample containing the retroviruses through the filtration medium such that the retroviruses are retained by the filtration medium.

2. The method of claim 1, wherein the porous nonofiber mat exhibits a mean flow bubble point, as tested with isopropanol, from 100 to 150 psi.

3. The method of claim 1, wherein the filtration medium has a thickness from about 1 µm to about 500 µm.

4. The method of claim 1, wherein the porous nonofiber mat has a thickness from 1 µm to 50 µm.

5. The method of claim 1, wherein the retrovirus is Human Immunodeficiency Virus (HIV).

6. The method of claim 1, wherein the retrovirus is Human T-cell leukemia virus (HTLV).

7. The method of claim 1, wherein the polymer is selected from the group consisting of polyimide, aliphatic polyamide, aromatic polyamide, polysulfone, cellulose acetate, polyether sulfone, polyurethane, poly(urea urethane), polybenzimidazole, polyetherimide, polyacrylonitrile, poly(ethylene terephthalate), polypropylene, polyaniline, poly(ethylene oxide), poly(ethylene naphthalate), poly(butylene terephthalate), styrene butadiene rubber, polystyrene, poly(vinyl chloride), poly(vinyl alcohol), poly(vinylidene fluoride), poly(vinyl butylene) and copolymers, derivative compounds, or blends thereof.

8. The method of claim 1, wherein the polymer comprises an aliphatic polyamide.

9. The method of claim 1, wherein the polymer comprises a blend of polymers or copolymers.

10. The method of claim 1, wherein the porous nanofiber mat is disposed on a porous support.

11. The method of claim 10, wherein the porous support comprises one or more layers selected from the group consisting of spunbonded nonwovens, meltblown nonwovens, needle punched nonwovens, spunlaced nonwovens, wet laid nonwovens, resin-bonded nonwovens, woven fabrics, knit fabrics, paper, and combinations thereof.

12. The method of claim 1, wherein the porous nanofiber mat has a fiber diameter from about 25-30 nm.

13. The method of claim 1, wherein the porous nanofiber mat has a fiber diameter from about 10-100 nm.

14. The method of claim 1, wherein the porous nanofiber mat has a liquid permeability of at least about 300 LMH/psi.

15. The method of claim 2, wherein the porous nanofiber mat has a fiber diameter from about 25-30 nm.

16. The method of claim 2, wherein the porous nanofiber mat has a fiber diameter from about 10-100 nm.

17. The method of claim 2, wherein the porous nanofiber mat has a liquid permeability of at least about 300 LMH/psi.

18. The method of claim 4, wherein the porous nanofiber mat has a fiber diameter from about 25-30 nm.

19. The method of claim 4, wherein the porous nanofiber mat has a fiber diameter from about 10-100 nm.

20. The method of claim 4, wherein the porous nanofiber mat has a liquid permeability of at least about 300 LMH/psi.

* * * * *

UNITED STATES PATENT AND TRADEMARK OFFICE
CERTIFICATE OF CORRECTION

PATENT NO. : 9,623,352 B2  
APPLICATION NO. : 13/194227  
DATED : April 18, 2017  
INVENTOR(S) : Onur Y. Kas et al.

Page 1 of 1

It is certified that error appears in the above-identified patent and that said Letters Patent is hereby corrected as shown below:

In Column 14, Line 15, in Claim 2 delete "nonofiber" and insert -- nanofiber --, therefor.

In Column 14, Line 20, in Claim 4 delete "nonofiber" and insert -- nanofiber --, therefor.

Signed and Sealed this  
Fifth Day of September, 2017

Joseph Matal  
*Performing the Functions and Duties of the*  
*Under Secretary of Commerce for Intellectual Property and*  
*Director of the United States Patent and Trademark Office*